United States Patent [19]

Foster et al.

[11] Patent Number: 5,879,924

[45] Date of Patent: Mar. 9, 1999

[54] IMMORTALIZED CELL LINES FOR VIRUS GROWTH

[75] Inventors: Douglas N. Foster; Linda K. Foster, both of Roseville, Minn.

[73] Assignee: Regents of the University of Minnesota

[21] Appl. No.: 941,849

[22] Filed: Sep. 30, 1997

Related U.S. Application Data

[63] Continuation of Ser. No. 696,200, Aug. 13, 1996, Pat. No. 5,672,485.

[51] Int. Cl.$^6$ ........................................................ C12N 7/00
[52] U.S. Cl. ......................................... 435/235.1; 435/349
[58] Field of Search ................................. 435/40.51, 349, 435/172.3, 172.1, 235.1; 424/94.63, 85.2

[56] References Cited

PUBLICATIONS

C.F. Boerkoel et al., "A New Defective Retroviral Vector System Based on the Bryan Strain of Rous Sarcoma Virus", *Virology*, 195(2)669–679 (1993).

Boyer et al., "Sequence and biological activity of chicken snoN cDNA clones", *Oncogene*, 8 457–466 (1993).

L.B. Crittenden et al., "Host Gene Control of Endogenous Avian Leukosis Virus Production", *Virology*, 57 128–138 (1974).

L. Curatolo et al., "Culture Conditions Induce the Appearance of Immortalized $C_3H$ Mouse Cell Lines", *In Vitro*, 20 597–601 (1984).

Foster et al., "Immortalization of Chicken Embryo Fibroblastic Cells", $84^{th}$ *Annual Meeting of the Poultry Science Assoc., Inc.*, Edmonton, Alberta, Canada, Aug. 14–18, 1995, 74 (Suppl. 1) 1995.

Federspiel et al., "Effects of the gag Region on Genome Stability: Avian Retroviral Vectors That Contain Sequences from the Bryan Strain of Rous Sarcoma Virus$^1$", *Virology*, 203(2) 211–220 (1994).

Givol et al., "Overexpression of human p21$^{waf1/cip1}$ arrests the growth of chicken embryo fibroblasts transformed by individual oncogenes", *Oncogene*, 11(12) 2609–2618 (1995).

Hamburger et al., "Soft–Agar Cloning of Cells From Patients With Lymphoma", *Prog. Clin. Biol. Res., Cloning of Human Tumor Stem Cells*, 48 43–52 (1980).

Harvey et al., "p53 alteration is a common event in the spontaneous immortalization of primary BALB/c murine embryo fibroblasts", *Genes and Development*, 5 2375–2385 (1991).

M. Hill et al., "Isolation of a Line of Immortal Chicken Embryo Fibroblasts after Transfection with Nuclei of Rous Sarcoma Virustransformed Chinese Hamster Cells", *Experimental Cell Research*, 156, 127–139 (1985).

B. Kressner et al., "Use of an Image Analysis System to Count Colonies in Stem Cell Assays of Human Tumors", *Prog. Clin. Biol. Res., Cloning of Human Tumor Stem Cells*, 48 179–193 (1980).

Pereira–Smith et al., "Genetic analysis of indefinite division in human cells: Identification of four complementation groups", *Proc. Natl. Acad. Sci. USA*, 85 6042–6046 (1988).

Pereira–Smith et al., "Hybrids From Fusion of Normal Human T Lymphocytes With Immortal Human Cells Exhibit Limited Life Span", *J. Cell Physiol.*, 144 546–549 (1990).

S. Salmon, "Morphologic Studies of Tumor Colonies", *Prog. Clin. Biol. Res., Cloning of Human Tumor Stem Cells*, 48 135–151 (1980).

Smith et al., "Replicative Senescence: Implications for in Vivo Aging and Tumor Suppression", *Science*, 273 63–67 (1996).

*Primary Examiner*—James Ketter
*Assistant Examiner*—Irem Yucel
*Attorney, Agent, or Firm*—Mueting, Raasch & Gebhardt, P.A.

[57] ABSTRACT

This invention relates to the production and use of immortalized cell lines from primary chicken embryonic fibroblasts. The cells are useful as substrates for virus propagation, recombinant protein expression and recombinant virus production.

8 Claims, No Drawings

IMMORTALIZED CELL LINES FOR VIRUS GROWTH

CROSS-REFERENCE TO RELATED APPLICATION

This is a continuation of application Ser. No. 08/696,200, filed Aug. 13, 1996 (now U.S. Pat. No. 5,672,485), which is incorporated herein by reference.

FIELD OF THE INVENTION

This invention relates to the fields of cell biology and virology. In particular this invention relates to the use of immortalized cells for virus propagation.

BACKGROUND OF THE INVENTION

In 1931 Alice Miles Woodruff and Ernest Goodpasture introduced a new method for cultivating viruses. They reported that the virus of fowl pox could be grown on the chorioallantoic membrane of developing chick embryos. Lesions containing the virus appeared on the membrane after virus inoculation. The egg was relatively cheap and readily obtainable as compared to animals which were the substrate for early virus studies. The egg has a variety of cells and membranes susceptible to infection by different viruses and can be kept in a controlled, stable environment. Chick embryos have contributed in an important way to the development of virology by conveniently providing a variety of cell types susceptible to many viruses.

While the egg supports the replication of a variety of virus strains, methods for infecting the eggs and maintaining virus growth are time consuming and cumbersome. For example, for chorioallantoic membrane inoculation, a hole is first drilled through the eggshell and shell membrane. The shell over the air sac is perforated causing air to enter between the shell membrane and the chorioallantoic membrane, creating an artificial air sac, where the sample is deposited. The sample contacts the chorionic epithelium and the virus grows as lesions on the membrane. Not unexpectedly, the use of eggs for virus replication has diminished with the advent of cell culture techniques.

A variety of cells can be grown in vitro. Cell cultures are easy to maintain and can be kept in a highly controlled environment as compared to eggs. However, there are still virus strains that appear to grow better in embryonated egg cells than in cultured cells. In addition, many cultured cell lines carry endogenous infectious agents including mycoplasmas, low level bacterial contaminants, endogenous viruses, and the like. Some of the cell types that are the most efficient at supporting virus replication have problems for viral stock production in that the cells contain endogenous virus. The endogenous virus is either replicating at a low level or can be activated when the cells are infected with a second virus strain. For example, rodent cells are known to carry endogenous viruses and electron microscopy of rodent cells in culture often demonstrates the existence of identifiable viral particles within the cells. Contaminated cell lines cannot be used as substrates for commercial live or inactivated vaccines.

For some viruses the method of choice for viral replication is the embryonated chicken. For example, human influenza virus, rabies, Canine Distemper virus, Marek's disease virus, Reovirus and Fowl Pox virus are viruses that are preferentially grown in embryonated eggs because the egg supports high titer virus stock growth or in primary cells dervied from the embryonated eggs. In other cases, viruses are grown in eggs because there is a need for certifiable virus free cell substrates.

Primary cell cultures are cultures of cells that are freshly isolated from intact tissues. These cells are often a good source of virus free material and are well suited as host cells for virus replication. Primary cells are not always efficient at replicating virus and primary animal cells exhibit a limited life span in culture, eventually undergoing senescence. At senescence the cells cease to divide and die out in a matter of time. The ability of cells to divide over time in culture is dependent on several parameters including the species of origin of the cell and the age of the tissue when it was placed in culture. Cells that undergo senescence cannot be maintained in culture for long periods of time and therefore are not useful reproducible hosts for the growth of commercial virus stocks.

Some primary cells escape senescence and acquire the ability to become immortal. Rodent cells appear to undergo spontaneous immortalization quite easily (Curatolo et al. *In Vitro* 20:597–601, 1984) but normal human and avian cells have rarely, if ever, been shown to be capable of spontaneous immortalization (Harvey, et al. *Genes and Development* 5:2375–2385, 1991; Pereira-Smith, *J. Cell Physiol* 144:546–9, 1990; Smith et al. *Science* 273:63–67, 1996). There are a variety of reasons why a particular population of cells would undergo immortalization. Cells can be induced to undergo immortalization following exposure to agents known to induce gene mutations. Some individuals postulate that cessation of growth, related to senescence, is dominant to immortalization and events that inactivate growth-restraining genes can result in immortalization (Pereira-Smith et al., *Proc. Natl. Acad. Sci. (USA)* 85:6042–6046, 1988).

The availability of immortalized, virus free cells can eliminate or reduce the use of primary animal tissue cultures. Primary cultures are generally ill-defined cell populations and are often contaminated. These cultures often fail to meet regulatory requirements for commercial vaccine production. Primary cultures of cells can be contaminated with Circodnaviridae (e.g., Chickenenima Virus) or Egg Drop Syndrome virus. For example, Marek's Disease vaccine (a live virus vaccine) can be grown as virus stocks in duck eggs for poultry vaccination. In 1976, flocks of chickens receiving the vaccine showed evidence of Egg Drop Syndrome, caused by a duck adenovirus that is believed to have contaminated the vaccine stock and became adapted to growth in chickens.

In the vaccine industry, regulatory requirements for product safety, consistency and potency are driving companies to pursue cell lines as the best alternative to the current practice of using egg-based and primary cell vaccine substrates. Concerns for safety and consistency are shared by manufacturers of both human and animal vaccine products due to an increasingly stringent regulatory environment regarding vaccine substrates in both the United States and Europe. The identification of suitable cells for virus growth to replace embryonated eggs is also favored in view of US Government Principles for the Utilization and Care of Vertebrate Animals in Testing, Research, and Training and the Animal Welfare Act (7 U.S.C. § 2131) stating, in part, that in all cases, methods such as in vitro biological systems should be considered in lieu of in vivo animal model systems. There is a need for cells that are virus free and support exogenous virus growth to generate animal vaccine products.

SUMMARY OF THE INVENTION

This invention relates to the identification of spontaneously immortalized chicken fibroblast cell lines and to methods for obtaining the cell lines. In particular, this invention relates to a spontaneously immortalized cell line derived from primary chicken embryonic fibroblasts having the characteristics of the spontaneously immortalized cell line UMNSAH-DF1 that is deposited with the ATCC under the terms and conditions of the Budapest Treaty. In addition, this invention relates to cultures of these cells and to immortalized subclones of the immortalized cell line that support virus replication.

In one aspect of this invention the immortalized cells of this invention contain virus and in another the immortalized cells of this invention contain at least one vector capable of directing expression of recombinant protein in the cells. In one embodiment the cells of this invention express recombinant protein and in another aspect of this invention the vector contained in the cells of this invention encodes at least a portion of a recombinant virus. In another embodiment the vector is a retroviral vector.

In another aspect of this invention a method is disclosed for producing an immortalized cell line from chicken embryonic fibroblasts comprising the steps of: growing primary chicken embryonic fibroblasts in culture; passaging the fibroblasts in culture until they begin cell senescence; concentrating the cells during cell senescence to maintain about 30% to about 60% culture confluence; identifying foci of non-senescent cells; and growing the non-senescent cells for greater than 30 passages.

In yet another aspect of this invention a method is disclosed for growing virus in a cell comprising the steps of: growing a spontaneously immortalized cell line derived from primary chicken embryonic fibroblasts in culture; infecting the cells with virus; allowing the virus to replicate in the cells; and collecting virus that replicated in the cells.

DETAILED DESCRIPTION OF THE PREFERRED EMBODIMENTS

At present there are essentially no non-viral, non-viral protein or non-chemically transformed avian cell lines available. Primary cell lines are cumbersome to continually generate for virus stock production and must be separately validated as contaminant free reservoirs for virus growth. This invention discloses the immortalization of chicken embryo fibroblastic (CEF) cells including cells derived from East Lansing Line (ELL-0) chicken embryos.

The term immortalization is used herein to refer to non-rodent cells capable of growing in culture for greater than 30 passages that maintain a doubling time in culture of about 1 to about 2 days and have been in continuous culture for greater than about 6 months. Avian cells are generally considered immortalized after about 20 to about 25 passages in culture. Immortalized cells are differentiated from transformed cells in that unlike transformed cells, immortalized cells are density dependent and/or growth arrested (e.g., contact inhibited). Transformed cells are capable of growth in soft agar and are usually able to form tumors when injected into laboratory animals. The cells of this invention are useful as reservoirs for growing virus or for expressing recombinant protein or virus particularly where it is important that the cells do not harbor contaminating virus or viral protein. The cells are also useful for studying the underlying mechanisms of cellular senescence and immortalization.

Chicken Embryo Fibroblastic (CEF) primary cells from 10 day old ELL-0 eggs were obtained by taking the embryonic torso of the 10 day old embryos, mincing the tissue and placing the cells in culture. Fertilized eggs are available Hy-Vac (Adel, Iowa). The eggs and their layers were certified by the supplier as negative for Avian influenza (Type A), Avian reovirus, Avian adenoviruses (Groups I-III), Avian encephalomyelitis virus, Fowl pox, Newcastle disease virus, Paramyxovirus (Type 2), Mycoplasma, Salmonella and other infectious agents known to infect poultry stock. Isolation of primary cells and identification of immortalized cells is provided in Example 1.

The cells were identified because at the time of the discovery of the immortalized line, cell populations were being selected to study the effects of cell senescence. Human and avian cells are known to be some of the most difficult cells to immortalize under tissue culture conditions. Unlike rodent cells, there are no peer-reviewed reports of methods for immortalizing human or chick fibroblasts from normal donors (Smith, et al. *Science* 273:63–67, 1996). In avian fibroblasts, untreated cells typically last only 20–25 passages. That is, by 30 passages primary cultures of these avian cells are dead or dying. As disclosed in this invention, to reach 20 passages, the cells were passed and concentrated (see Example 1) between about passage 12 up to about passage 20 onto smaller plates as needed. Foci of more rapidly growing cells were observed and these foci were isolated using cloning rings (Bellco Glass, Inc. Vineland, N.J.) and expanded in culture.

Senescence is defined herein as cells having population doublings of about 0.5 population doublings or less per day. For this invention, immortalized cells are cells in culture for more than 30 passages, growing at a population doubling rate (as determined by total cell counts and viable cell counts per day using trypan blue exclusion) of about between 0.6 to about 1.2 population doublings per day and preferably between about 0.7 to about 1.0 population doublings per day while exhibiting contact inhibition, density dependence and a normal cell morphology.

The cells obtained from the originally identified foci, as described in Example 1, have undergone greater than 400 (population doublings) and greater than 160 passages. The term foci is used herein to refer to clusters of morphologically uniform cells that can be distinguished from the morphology of the cells around them. These foci of cells can be readily removed and subcloned for further study. The cells of this invention have continued to double every 22–24 hrs. The cells were contact inhibited, reverse transcriptase negative (see Example 2), density dependent arrested, aneuploid (as observed by chromosome spread analysis under oil emersion microscopy the karyotype was a mixture of diploid/tetraploid karyotypes with some cells displaying an apparent translocation of chromosome 1), and grow to high plating densities of between $1.1-1.9\times10^5$ cells/cm$^2$. No multinucleated giant cells were observed. The cells have a uniform phenotype. The cells also maintain a characteristic pattern of rapid growth which is important for virus propagation.

The cells were nontransformed as demonstrated by their inability to grow in soft agar assays (see Example 3). In addition, the cells did not produce tumors when injected into the wings of chickens (see Example 4). Exemplary cells of this invention were designated UMNSAH-DF1 cells and are deposited with the American Type Culture Collection (ATCC), 12301 Parklawn Drive, Rockville Md., 20852 as accession number CRL 12203 deposited on Oct. 11, 1996 under the terms and conditions of the Budapest Treaty.

This invention also relates to the immortalized chicken embryonic fibroblast cells of this invention in culture and to subclones of the immortalized cells of this invention. For example, the cells of this invention are identified as spontaneous immortalized cells. The cells are obtained from knot n virus-free, known chemical contaminant-free layers (hens producing the embryonic tissues that are the source of this invention) and the embryonic tissues used to produce the cells of this invention are also chemical contaminant-free (i.e, free from treatment by known carcinogens or other agents known to transform rodent cells) and free from known virus. Once the immortalized cells of this invention are in culture, it is possible to further subclone the cells to select for other physiological parameters that may vary in the cell population while still maintaining contact inhibition and susceptibility to virus infection.

Cells were tested for their ability to replicate HVT (Herpesvirus of Turkeys), avian herpesvirus (serotype III), Fowl Pox virus, and reovirus. Cells can be tested for their ability to replicate Circodnavirideae, chicken HSV serotype II for a variety of other viruses and have been tested as a substrate for transfection. The cells were useful for propagating both avian and non-avian viruses. Example 5 details methods for propagating HVT, Fowl Pox virus and reovirus. The cells are useful as a substrate for viral production, and in particular the cells are useful for retrovirus production since the cells and their layers (i.e., their mothers) did not have detectable retrovirus infections. The cells are able to support the replication of Avian Sarcoma Leukemia Virus and Rous Sarcoma Virus.

To produce virus stock, the cells of this invention can be seeded into tissue culture flasks, roller bottles, stir culture, into hollow fiber reactors or other mass culture systems. For roller bottle virus propagation, the cells are seeded at about $2–5 \times 10^4$ cells/cm$^2$ of surface area. The multiplicity of infection (ratio of infectious virus particles to cells) to initiate virus stock growth will vary depending on virus strain. Those skilled in the art of virology and skilled in the growth of particular viruses and strains of viruses will be able to maximize virus stock yield through the standard manipulation of the multiplicity of infection, temperature, media variations, and the like, without undue experimentation.

Methods for harvesting the virus after infection to obtain infectious virus stock also varies with virus strain. Enveloped viruses egress into the culture media more slowly than non-enveloped virus. Stocks of virus can be obtained from the culture media alone or from cell lysates pooled with the conditioned media. For lytic viruses (those efficient at lysing a cell during virus egress), harvesting the conditioned culture media (e.g., spent media containing virus) after a gentle centrifugation step to remove cell debris is sufficient. Again, methods for harvesting and saving virus from a wide range of virus strains are well known in the art.

There are a variety of methods, also all known in the art, for quantitating virus growth from a culture of cells. For example, the titer of a virus stock for members of the Herpesvirus family and for a variety of viruses producing foci of cytopathology on a cell monolayer surface are readily quantitated by plaque assay (as plaque forming units/ml of culture fluid or as plaque forming units/dose for vaccine inoculum virus quantitation) or as tissue culture infectious dose-50 (TCID$_{50}$). Rapidly lytic viruses are better quantitated by TCID$_{50}$ as the dose or dilution of virus stock capable of infecting 50% of the cultures in a defined time period. Methods for growing and quantitating virus are known in the art and sources for teaching virus quantification methods are found in Fields, et al. (eds) *Fundamental Virology* 1991, Raven Press, New York or in Mandell, et al. (eds.) *Principles and Practice of Infectious Diseases*, 1985, John Wiley & Sons, New York.

In addition to supporting virus growth, the cells of this invention can be used as packaging lines to produce recombinant virus, including retrovirus. The cells can also be used to produce recombinant proteins, including viral proteins, and the like. Methods for incorporating nucleic acid encoding recombinant protein into a nucleic acid vector under the control of regulatory elements capable of directing expression of a protein in a eukaryotic cell, such as the immortalized cells of this invention, are well known in the art. Expression vectors are replicable nucleic acid fragments that can direct expression of a recombinant protein. Many expression vectors, including retroviral vectors, are available in the art through journal publications and commercial suppliers. Replicable expression v ector components generally include, but are not limited to, one or more of the following: an origin of replication, one or more marker genes, enhancer elements, promoter elements, optional signal sequences and transcription termination sequences. The selection or marker genes encode protein that serves to identify a population of transformed or transfected cells. Typical selection genes encode proteins that confer resistance to antibiotics or other toxins, complement auxotrophic deficiencies or supply critical nutrients not available from complex media.

Expression vectors having nucleic acid encoding recombinant protein are transfected into the cells and are used to direct expression of the recombinant protein in the immortalized cells of this invention. The vector preferably can encode any recombinant protein capable of expression in chicken embryonic fibroblast cells, including, but not limited to, virus protein, including reverse transcriptase and/or viral structural protein. Examples of vectors to produce recombinant protein in a cell include retroviral vectors to produce tumor suppressive protein, or viral structural protein such as those disclosed by Givol, et al. *Oncogene* 11(12):2609–2618, 1995, Givol, et al. *Cell Growth & Differentiation* 5(4):419–429, 1994, Federspiel, et al. *Virology* 203(2):211–220, 1994 and Boyer, et al. *Oncogene* 20:457–66, 1993.

The cells of this invention can serve as substrate to express recombinant virus, including, but not limited to recombinant retrovirus. The cells of this invention are suitable to serve as packaging cell lines for genetically engineered virus useful for gene therapy, or the like. Constructs and methods for using a particular cell line as a packaging cell line are known in the art. For example, Boerkoel, et al. (*Virology* 195(2):669–79, 1993) discloses methods for packaging virus using primary chicken embryonic fibroblasts as the packaging cell line. These same methods can be used to package virus in the immortalized cells of this invention.

Since most avian cell lines and all transformed avian cells as well as virtually all mouse transformed cell lines either contain viral contaminants such as endogenous virus or produce viral protein, they are not suited for the production of human or animal vaccines. The cells cannot be used to produce recombinant protein because the endogenous contaminants can contaminate purified recombinant protein preparations. Advantageously, the cells of this invention provide a suitable alternative to these problems.

The cells of this invention can also serve as a substrate for supporting virus growth from other cells. These other cells include primary cells, or cultured cells that show improved growth or longevity in culture in the presence of other cells or in the presence of extracellular matrix proteins such as collagens, laminins, and the like. In one embodiment, cells are mixed with virus and then mixed with the cells of this invention preferably in a ratio of cells: to cells of this invention of about between 1:5 cells to about 1:20 cells and more preferably in a ratio of about 1:10 (1 cell to about 10 cells of this invention). The mixed cells are then placed into culture. In a second embodiment the cells are mixed with virus and plated onto the surface of the immortalized cells of this invention are already attached to a tissue culture surface. The cells of this invention serve as a support for the other cells and, without intending to limit the scope of this invention, the cells of this invention can supply growth factors and the like as well as extracellular matrix components, and the like to support the other cells while they are producing virus. Example 6 provides an example of the use of the cells of this invention as a cell substrate.

Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Establishment of Spontaneous Chicken Fibroblast Cell Line

Two dozen ELL-0 eggs were ordered from East Lansing USDA poultry stocks. The eggs were incubated in a sterilized isolated incubator for 10 days and were processed for primary cultures. Embryonic tissue was dissociated using a trypsin/EDTA solution and plated in DMEM media (Gibco) containing 10% fetal calf serum (Gibco). 1% antibiotic/antimycotic (Gibco) containing and 2 mM L-glutamine (Gibco). The dissociated cell suspension was collected in a 50 ml centrifuge tube containing 10% ml fetal bovine serum to inactivate the trypsin and centrifuged at 700 xg for 10 minutes.

The cells were resuspended in 10 ml Dulbecco's modified Eagles's medium enriched with 36 µg/ml insulin (Sigma), 1.6 µg/ml transferrin (Sigma, St. Louis, Mo.), 2 mM L-glutamine, 10% fetal calf serum, 1% antibiotic/antimycotic solution and pipetted into a 25 cm$^2$ corning tissue culture flask and incubated at 40.5° C. in 5% $CO_2$, 95% air. After 24 hours of incubation, the media was changed. The primary culture contained numerous explants with centers of epithelial-like cells and radiating fibroblasts.

Cultures were allowed to grow to confluency (5 days) and were removed from the plates using a trypsin/EDTA solution (0.05% trypsin and 0.02% ethylene diamine tetra acetic acid (EDTA) in PBS) and replated for second passage. At second passage some of the cells were frozen in a conditioned media containing 50% DMEM media, 12% DMSO and 38% fetal calf serum. These cells were frozen in the vapor phase liquid nitrogen for 24 hours then transferred to the aqueous liquid nitrogen for long term storage.

Cells at second passage (P2) were replated at a seeding density of $2.7 \times 10^4$ cells/cm$^2$. The cells were sub-cultured for several months. The cultured fibroblasts grew rapidly for 8 to 9 passages, then began to slow down with significant cell death. During crises, the cells were passed using an ATV solution (8 gm/l NaCl, 0.4 gm KCl, 1 gm dextrose, 0.58 gm $NaHCO_3$, 0.5 gm trypsin (Difco 1:250), 0.2 gm versene (disodium salt) in 1000 mL). Cells were grown in Dulbecco's modified Eagles's medium enriched with 36 µg/ml insulin (Sigma), 1.6 µg/ml transferrin (Sigma), 2 mM L-glutamine, 10% fetal calf serum and 1% antibiotic/antimycotic solution. It was noted that the majority of the cells at passage 11 (P11) were dead or dying; however, a small subpopulation of cells appeared to be healthy fibroblasts. The P11 cells remained on the dish for four weeks with refeeding every three days with fresh media. Some cells were frozen and the remaining cells were concentrated into a smaller area and were allowed to grow another two weeks before they were confluent enough for a second subculturing. By P15, the cells were appearing to be more homogeneous in cellular morphology and were growing at a rate of 0.32 population doublings per day. By P20, the population doublings increased to about 0.7 to about 0.8 population doublings per day. At this time the cells appeared to have a very uniform morphology. The cells were denoted UMNSAH/DF #1 and have been in continuous culture for over nineteen months. The cells are currently at passage 160. Cells were frozen (as above) and thawed from P5. The subcloned cells were expanded and the reproducibility of the method was confirmed through the identification of other clones. Several more subclones were obtained by P11.

EXAMPLE 2

Testing cells for virus contaminants

The cells of this invention are tested for viral contaminants using PCR to identify contaminating nucleic acid fragments. There are a wide variety of commercially available test kits for a variety of viruses that can be used to determine whether the cells of this invention contain contaminating virus. Similarly, there are commercially available tests to detect viral antigen (e.g., commercially available ELISA assays and the like), where the antigen is derived from a variety of different viruses. These tests can be used on the cells of this invention using routine experimental techniques to demonstrate that the cultures are free of contaminating virus.

In one series of tests, the cells were tested for reverse transcriptase activity. $1 \times 10^6$ cells from rapidly growing cultures were isolated in 4 ml. of media. The media was taken through several freeze thaws at −80° C. to lyse the cells. The media with lysed cells were layered over a 10% glycerol gradient. The gradient was spun for 60 minutes at 40,000 rpm using an SW40 rotor (Beckman Instruments, Palo Alto, Calif.). Virus particles, if present were pelleted. The media was discarded and the pellet was resuspended in 20 µl of Nonidet P-40 (Sigma Chemical Co., St. Louis, Mo.).

An eppendorf tube was heated at 41° C. 5 µl of sample was added to 45 µl of reverse transcriptase cocktail containing 45 mM Tris, pH 7.8, 2 mM 2-β mercaptothanol, 2 mM manganous acetate, 0.1% Triton X-100, 10 µM each dATP, dCTP, dGTP (Boehringer Mannheim Biochemical, Indianapolis, Ind.), 2.4 µg polyA (Sigma), 60 ng primer dT 12–19 (Pharmacia), 0.4 µCi/reaction $^3$H thymidine triphosphate (15,000 to 28,000 cpm/pmole activity, Amersham).

The reaction was incubated for one hour at 41° C. A negative control included 5 µl of dd$H_2$0 and 45 µl of the cocktail. Two known positive controls were included with the assay. The assay was stopped by adding 1 ml of 10% trichloroacetic acid (TCA, Columbus Chemical Industries, Inc., Columbus, Wis.). The mixture was filtered through a Whatman GF/C glass 0.45 micron pre filter. Several washes were performed using 5% TCA. The filter was transferred to a Beckman Instruments Scintillation Counter using scintillation vials containing 5 mls of scintillation counting fluid. Samples were counted on a 050 to 600 window setting. An increase of threefold counts over the cocktail background (neg. control) was considered positive.

The primary cultures tested negative for reverse transcriptase as did the immortalized cells obtained in this

EXAMPLE 3

Soft Agarose Colony Formations Assay to Assess Tumorigenic Potential of Cells To test for tumorigenic potential, the cells were tested for growth in soft agar. A soft agarose base was made by mixing 12 ml of a 2% agarose solution (that had been autoclaved and cooled to 56° C.) in 21.6 mls of enriched McCoy's 5A medium [Gibco, 120 mls fetal calf serum (heat inactivated, 5 mls Na pyruvate (2.2% stock), 1 ml L-serine (21 mg/ml stock), 5 mls L-glutamine (200 mM stock), 12.5 mls Hepes (1M stock)], 5.9 mls Asparagine (4.4 mg/ml filtered sterilized stock). Seven mls of warm media/agarose was poured onto a 100 mm² tissue culture dish and allowed to solidify at room temperature in a tissue culture hood for 1 hr.

Cells were removed from actively growing cultures (about 40% to about 70% confluent) by trypsinization to achieve a single cell suspension in fresh DMEM media containing 10% fetal calf serum (with L-glutamine and antibiotics-antimycotic). Approximately $1 \times 10^6$ cells was added to 4.25 ml of DMEM media containing 10% fetal calf serum, 0.75 ml of 1% agarose, and 50 μl 2β-mercaptoethanol. Care was needed to be certain that the warm media/agarose was at 42° C. before adding the cells. Quickly, 5 ml of the above cell suspension was overlaid on the agarose plates.

Cells were grown at 37° C. in a 5% $CO_2$ 95% air incubator and observed for 35 days. Duplicate plates were stained with 3 p-nitrophenyl-5-phenyl tetrazolium chlorite (INT stain) and examined at days 0, 5, 10, 15,20, 30 and 35 for colony formation and growth. All stained colonies greater than 60 μm were considered positive.

All cells tested negative. Further information related to the soft -agar assay is available from Hamburger et al., *Prog Clin. Biol. Res., Cloning of Human Tumor Stem Cells*, 48, 43–52 (1980); S. Salmon, *Prog. Clin. Biol. Res., Cloning of Human Tumor Stem Cells*, 135–151 (1980); and B. Kressner et al., *Prog. Clin. Biol. Res., Cloning of Human Tumor Stem Cells*, 179–193 (1980).

EXAMPLE 4

Tumorgenicity of Immortalized cells

Under the guidelines outlined in the University of Minnesota Animal Usage Protocol (protocol #950300-1, March 1995–December 1996) cells were injected into test animals to determine whether or not the cells were tumorigenic.

Actively growing cells were removed from cell culture plates and were injected into six SPAFAS line adult chickens (Hy-Vac, Adel. Iowa). Subcutaneous injections of $4 \times 10^6$ cells were introduced into the wing webs of the chickens. The sites of injection were examined weekly for 3.5 months. No tumors were observed at the injection site for any of the transfected cells produced to date with all animals remaining healthy. The experiment demonstrated that the immortalized cells were nontumorigenic.

EXAMPLE 5

Ability of Cells to Support Virus Growth

The cells were seeded into roller bottles at $5.0 \times 10^5$ cells/cm². The cells were allowed to attach for 24 hours and a control was harvested for cell counts. Cells were grown for virus infection in DMEM (4.5 g/L glucose), 4% Fetal Bovine Serum, 2 mM L-Glutamine, 50 mg/L Gentamicin. Cells were infected at a multiplicity of infection of 0.0006 HVT virus particles per cell. The roller bottles were watched daily for progression of CPE. The bottles were harvested at 46 hs. post infection when there was approximately 50% CPE. HVT infected cells were frozen in growth medium with 10% DMSO at a concentration of $2.0 \times 10^7$ cells/ml. Titers of HVT were quantitated by plaque assay. Virus was serially diluted in growth media and placed onto confluent monolayers of permissive cells. Cultures were incubated for a designated time and the cells were fixed and stained. Plaques on the monolayers were counted and virus titer was expressed as plaque forming units per dose.

These cells were also tested for their ability to support reovirus production. $2.5 \times 10^8$ cells were infected with WSS-Reo 1733 strain of Reovirus having a titer of 8.2 $TCID_{50}$/ml. Cells were infected at a multiplicity of infection of 0.005, 0.001 or 0.0005 infectious virus particles/cell. Infected cells were grown in roller bottles and tested at 48, 64 and 72 hours after infection to demonstrate productive viral growth.

EXPERIMENT 6

Use of Transfected Skin Cells as a Cell Substrate

The cells of this invention are useful as a substrate for supporting virus replication of primary cells. In these experiments the immortalized cells are mixed with primary cells. In one study the primary cells are infected and mixed with the immortalized cells and placed in culture and in another study the primary cells are infected and placed onto the immortalized cells where the immortalized cells are already positioned as a lawn in the tissue culture flask. In one example the virus is Egg Drop Syndrome virus and the primary cells are primary chicken embryonic liver cells. In a second example the primary cells are endothelial cells, preferably kidney endothelial cells and the virus is infectious bronchitis virus. The preferred ratio of primary cells to immortalized cells is about 1:5 to about 1:20 and more preferably about 1:10. Virus titers from primary cells growing in the mixed cell population are higher than virus titers from primary cells in culture alone. The immortalized cells allow the primary cells to be used for virus propagation under commercial conditions.

All cited publications are incorporated by reference in their entirety into this text. Although the invention has been described in the context of particular embodiments, it is intended that the scope of coverage of the patent be limited only by reference to the following claims.

What is claimed is:

1. A method for growing virus from a first cell comprising the steps of:
    incubating a first cell with virus;
    combining the first virus with immortalized chicken cells obtained by growing primary chicken embryonic fibroblasts in culture,
        passaging the fibroblasts in culture until they begin cell senescence,
        concentrating the cells during cell senescence to maintain about 30% to about 60% culture confluence,
        identifying foci of non-senescent cells in the culture,
        isolating the non-senescent cells, and
        growing the non-senescent cells for greater than 30 passages; and
    isolating virus produced from the combination of the first cell and the immortalized chicken cells.

2. The method of claim 1 wherein the virus is a retrovirus.

3. The method of claim 1 wherein the virus is a herpesvirus.

4. The method of claim 3 wherein the virus is Marek's disease virus.

5. The method of claim 1 wherein the virus is selected from the group consisting of fowlpox virus or reovirus.

6. The method of claim 1 wherein the immortalized cells are cells identified as ATCC deposit number CRL-12203.

7. A method for quantifying the amount of virus in a sample comprising the steps of:

preparing at least one serial dilution of a virus;

contacting a sample of virus from at least one dilution of virus with immortalized chicken cells obtained by:

growing primary chicken embryonic fibroblasts in culture, passaging the fibroblasts in culture until they begin cell senescence, concentrating the cells during cell senescence to maintain about 30% to about 60% culture confluence, identifying foci of non-senescent cells in the culture, isolating the non-senescent cells, and growing the non-senescent cells for greater than 30 passages; and quantifying the amount of virus present in the virus dilution.

8. The method of claim 7 wherein the immortalized cells are cells identified as ATCC deposit number CRL-12203.

* * * * *

UNITED STATES PATENT AND TRADEMARK OFFICE
CERTIFICATE OF CORRECTION

PATENT NO.   : 5,879,924
DATED        : March 9, 1999
INVENTOR(S)  : Foster et al.

It is certified that error appears in the above-identified patent and that said Letters Patent is hereby corrected as shown below:

<u>Title page,</u>
Item [21], Appl. No.:, delete "941,849" and insert therefor -- 08/941,849 --.

Item [63], Related U.S. Application Data, delete "696,200" and insert therefor -- 08/696,200 --.

<u>Column 5,</u>
Lines 1 and 2, after "obtained from" delete "knotn" and insert therefor -- known --.

<u>Column 6,</u>
Line 14, after "Replicable expression" delete "v ector" and insert therefor -- vector --.

<u>Column 8,</u>
Line 47, delete "mercaptothanol" and insert therefor -- mercaptoethanol --.

<u>Column 10,</u>
Line 55, after "combining the first" delete "virus" and insert therefor -- cell --.

Signed and Sealed this

Twenty-fifth Day of December, 2001

Attest:

Attesting Officer

JAMES E. ROGAN
*Director of the United States Patent and Trademark Office*